United States Patent [19]

Hara

[11] Patent Number: 4,948,577

[45] Date of Patent: Aug. 14, 1990

[54] COMPOSITION FOR EXTERNAL APPLICATION

[75] Inventor: Kenichi Hara, Onojo, Japan

[73] Assignee: Sansho Seiyaku Co., Ltd., Onojo, Japan

[21] Appl. No.: 129,252

[22] Filed: Dec. 7, 1987

[30] Foreign Application Priority Data

Sep. 25, 1987 [JP] Japan .................... 62-241881

[51] Int. Cl.$^5$ .............. A61K 7/021; A61K 7/44; A61K 7/135
[52] U.S. Cl. .................... 424/59; 424/60; 424/62; 424/63; 424/69; 514/460; 514/844; 514/845; 514/951
[58] Field of Search ............ 424/58, 59, 60, 62, 424/63, 69; 514/460, 844, 845, 951

[56] References Cited

U.S. PATENT DOCUMENTS

| | | | |
|---|---|---|---|
| 4,278,656 | 7/1981 | Nagai et al. | 424/62 |
| 4,369,174 | 1/1983 | Nagai et al. | 424/62 |
| 4,710,373 | 12/1987 | Nakamura et al. | 424/59 |

*Primary Examiner*—John W. Rollins
*Attorney, Agent, or Firm*—Jordan and Hamburg

[57] ABSTRACT

A composition for external application comprising kojic acid or a kojic acid derivative is characterized by formulating 4-(1,1-dimethylethyl)-4'-methoxydibenzoylmethan therein. The composition has the improved effects of inhibiting the formation of erythema and pigmentation caused by exposure to ultraviolet rays, preventing stains or freckles due to sunburn and preventing coloration after application, thus providing excellent compositions for external application as cosmetics, topical skin agents, etc.

8 Claims, No Drawings

COMPOSITION FOR EXTERNAL APPLICATION

BACKGROUND OF THE INVENTION

1. Field of the Invention

The present invention relates to compositions for external application comprising as an effective ingredient kojic acid or a kojic acid derivative which can inhibit erythema or pigmentation on the skin and prevent coloration of the compositions after external application.

2. Prior Art Statement

As substances for preventing formation of melanin on human skin, kojic acid and kojic acid derivatives are known. Skin coating agents comprising these substances as effective ingredients are also known. For example, these are whitening cosmetics comprising kojic acid as a whitening component (Published Unexamined Japanese Patent Application No. 3538/78 and Published Examined Japanese Patent Application No. 18569/81), whitening cosmetics comprising aliphatic carboxylic acid diesters of kojic acid or aliphatic carboxylic acid mono-esters of kojic acid as whitening components (Published Examined Japanese Patent Application Nos. 60801/86 and 9722/85), whitening cosmetics comprising esters of aromatic acids such as cinnamic acid, benzoic acid, etc. of kojic acid as whitening components (Published Examined Japanese Patent Application No. 10005/85), ointments for preventing formation of melanin comprising kojic acid as an effective ingredient (Published Examined Japanese Patent Application No. 10447/86), etc.

Further in order to prevent coloration of the kojic acid due to the passage of time, there are known cosmetics comprising kojic acid having formulated therein 2-hydroxy-benzophenone compounds (Published Unexamined Japanese Patent Application No. 108804/87).

As described above, kojic acid and a kojic acid derivative are extremely excellent substances that can inhibit the formation of melanin; the substances are known as skin coating agents used in cosmetics. When the substances are incorporated into cosmetics and skin agents for external application and applied to the skin, the substances exhibit the excellent effects of whitening and inhibiting the formation of melanin, and cause no irritation to the skin.

Even though pigmentation such as chloasma or the like is improved by the action of kojic acid, however, pigmentation once cured sometimes reverts to its original state due to the effects of ultraviolet rays when exposed to direct rays of the sun.

It is also pointed out that when the skin is exposed to strong outdoor direct rays of the sun with these agents for external application applied to the skin, the agents for external application are sometimes colored.

SUMMARY OF THE INVENTION

The present inventor has made extensive investigations in an attempt to obtain compositions for external application comprising kojic acid or a kojic acid derivative as an effective ingredient which inhibit erythema and pigmentation due to exposure to ultraviolet rays, enhance the prevention of strains or freckles caused by sunburn, prevent coloration upon use and not cause irritation to the human skin upon use. As a result, it has been found that by formulating 4-(1,1-dimethylethyl)-4'-methoxydibenzoylmethane in compositions for external application comprising kojic acid or a kojic acid derivative as an effective ingredient, neither erythema nor pigmentation appear on the skin after application of such compositions and coloration upon use can be prevented, even though the skin is exposed to ultraviolet rays, whereby the present invention has been accomplished.

DESCRIPTION OF THE PREFERRED EMBODIMENTS

The composition of the present invention for external application contains kojic acid or a kojic acid derivative which is known as a substance for inhibiting the formation of melanin. Examples of the kojic acid derivative include mono-fatty acid esters of kojic acid, for example, kojic acid monopalmitate, kojic acid monobutyrate, kojic acid mono-caprylate, kojic acid monostearate (disclosed in Published Unexamined Japanese Patent Application No. 77272/81), di-fatty acid esters of kojic acid, for example, kojic acid dipalmitate, kojic acid dibutyrate, kojic acid dioleate, kojic acid distearate (disclosed in Published Unexamined Japanese Patent Application No. 7776/81), kojic acid monocinnamoate, kojic acid monobenzoate (Published Unexamined Japanese Patent Application No. 33207/84), etc.

The composition of the present invention for external application can be used in cosmetics such as a cream, a cosmetic lotion, a pack, powders or the like, as well as quasi drugs for external application such as an emulsion, a lotion, a liniment, an ointment, etc. These preparations can be obtained by making the effective ingredients described above into preparations in a conventional manner using conventional bases.

4-(1,1-Dimethylethyl)-4'-methoxydibenzoylmethane used for preventing coloration of the composition of the present invention for external application comprising kojic acid or the kojic acid derivative is a sun shielding substance disclosed in Published Examined Japanese Patent Application No. 16258/86 and is commercially available under the trademark of "PARSOL 1789" by GIVAUDAN Co., Ltd. In the present invention, by formulating 0.01 to 5.0% (by weight) of this substance in the composition for external application based on the total amount, erythema and pigmentation of kojic acid or the kojic acid derivative caused by ultraviolet rays can be inhibited, the effect of preventing strains or freckles due to sunburn can be enhanced and the composition for external application does not undergo coloration upon use.

The composition of the present invention for external application may also appropriately contain, in addition to 4-(1, 1-dimethylethyl)-4'-methoxydibenzoylmethane, known UV absorbents such as benzophenone compounds, for example, 2-hydroxy-4-methoxybenzophenone, 2-hydroxy-4-methoxybenzo-phenone-5-sulfonic acid, 2,2',4,4'-tetrahydroxybenzophenone, etc.; UV absorbents such as phenyl salicylate, ethyl p-aminobenzoate, ethyl urocaniate, 2-(2-hydroxy-5-methylphenyul)-benzo-triazole, isopropyl p-methoxycinnamate, 2-ethylhexyl p-methoxy-cinnamate, etc.; or UV absorbents from plant extracts such as aloe extract, scutellaria root extract, shear butter, γ-orizanol, soybean oil, etc. to enhance the effect of the present invention.

The present invention will be described in more detail with reference to the examples below but is not deemed to be limited thereto.

Further, anionic substances such as sodium N-lauroyl-L-glutamate, sodium dl-pyrrolidonecarboxylate, etc.; cationic substances such as stearyl chloride trimethylammonium, cetyl chloride trimethylammonium, etc.; and antioxidants such as nicotinic amide, nicotinic acid, natural vitamin E, etc. may also be added to the composition.

Next, examples of the present invention and test examples on inhibiting erythema and pigmentation on the skin as well as prevention of coloration of the composition for external application are given below.

EXAMPLE 1

(cosmetic lotion)

A mixture of 1.00 g of polyoxyethylene-hardened castor oil (60 E.O), a trace amount of fragrance, 15.00 g of ethanol and 0.10 g of ethyl p-oxybenzoate was homogeneously stirred to dissolve the components. Separately, 0.10 g of citric acid, 0.30 g of sodium citrate, 0.50 g of sodium N-lauroyl-L-glutamate, 4.00 g of 1,3-butylene glycol, 0.50 g of kojic acid, 0.50 g of 4-(1,1-dimethylethyl)-4'-methoxydibenzoylmethane and 5.00 g of aloe extract as well as purified water to make a total of 100 g were homogeneously stirred to dissolve the components. The former solution was added to the latter solution and mixed to make a cosmetic lotion.

EXAMPLE 2

(emulsion)

A mixture of 0.50 g of polyoxyethylene-behenyl ether oil (20 E.O), 1.00 g of tetraoleate polyoxyethylene sorbitol (60 E.O), 1.00 g of oleophilic glycerin monostearate, 0.50 g of stearic acid, 0.50 g of behenyl alcohol, 1.00 g of avocado oil, 0.02 g of natural vitamin E, 0.20 g of ethyl p-oxybenzoate and 1.00 g of 4-(1,1-dimethylethyl)-4'-methoxydibenzoylmethane was heated to dissolve the components. Separately, 0.50 g of 2-hydroxy-4-methoxybenzophenone-5-sulfonic acid, 5.00 g of 1,3-butylene glycol, 0.10 g of carboxyvinyl polymer, 0.50 g of sodium N-lauroyl-L-glutamate and 50 g of purified water were heated to dissolve the components. The latter solution was added to the former solution. The mixture was stirred, emulsified and cooled.

To the thus obtained emulsion were added 0.50 g of kojic acid, a trace amount of fragrance and purified water to make a total of 100 g. The mixture was stirred and mixed to make an emulsion.

EXAMPLE 3

(cream)

Two grams of monostearate polyoxyethylene glycol (40 E.O), 5.00 g of self-emulsion-type glycerin monostearate, 5.00 g of stearic acid, 1.00 g of behenyl alcohol, 10.00 g of liquid paraffin, 10.00 g of glyceryl trioctanoate, 0.20 g of ethyl p-oxybenzoate and 0.50 g of 4-(1,1-dimethylethyl)-4'-methoxy-dibenzoylmethane were heated to dissolve the components. Separately, purified water was added to 5.00 g of 1,3-butylene glycol to make a total of 1.00 g. The mixture was heated to dissolve the components. The latter was added to the former followed by stirring, emulsifying and cooling.

To the thus obtained emulsion were added 1.00 g of kojic acid, a trace amount of fragrance and 8.00 g of purified water. The mixture was stirred and mixed to make a cream.

EXAMPLE 4

(cream)

One gram of monostearate polyoxyethylene sorbitan (60 E.O.), 1.50 g of tetraoleate polyoxyethylene sorbitol (60 E.O), 1.50 g of self-emulsion-type glycerin monostearate, 2.00 g of white bee's wax, 2.00 g of paraffin, 3.00 g of stearic acid, 3.00 g of behenyl alcohol, 12.00 g of shear butter, 0.04 g of natural vitamin E, 0.10 g of methylpolysiloxane, 0.20 g of ethyl p-oxybenzoate, 1.00 g of 4-(1,1-dimethylethyl)-4'-methoxy-dibenzoylmethane, 1.00 g of 2-ethylhexyl p-methoxycinnamate and 5.00 g of liquid paraffin were heated to dissolve the components. Separately, purified water was added to 5.00 g of 1,3-butylene glycol, 0.30 g of citric acid and 0.50 g of sodium N-lauroyl-L-glutamate to make a total of 1.00 g. The mixture was heated to dissolve the components. The latter was added to the former followed by stirring, emulsifying and cooling.

To the thus obtained emulsion were added 2.00 g of kojic acid and a trace amount of fragrance. The mixture was stirred and mixed to make a cream.

EXAMPLE 5

(pack)

One gram of polyoxyethylene behenyl ether (20 E.O), 2.00 g of tetraoleate polyoxyethylene sorbitol (40 E.O), 2.00 g of oleophilic glycerin monostearate, 3.00 g of behenyl alcohol, 25.00 g of squalane, 10.00 g of glycerin octanoate, 0.04 g of natural vitamin E, 0.20 g of ethyl p-oxybenzoate and 0.50 g of 4-(1,1-dimethylethyl)-4'-methoxydibenzoylmethane were heated to dissolve the components. Separately, 5.00 g of 1,3-butylene glycol, 1.50 g of sodium dl-pyrrolidonecarboxylate and 50 g of purified water were heated to dissolve the components.

The latter was added to the former followed by stirring, emulsifying and cooling. To the thus obtained emulsion were added 0.04 g of citric acid, 1.00 g of kojic acid and a trace amount of fragrance. Water was added thereto to make a total of 100 g in the form of a pack.

EXAMPLE 6

(powder)

Maltitol, 96.0 g, 1.0 g of octyldodecyl myristate, 2.0 g of kojic acid, 1.0 g of 4-(1,1-dimethylethyl)-4'-methoxydibenzoyl-methane and a trace amount of fragrance were homogeneously stirred and mixed to powders.

Test Example 1

(test on prevention of erythema and pigmentation)

(1) Test sample (a) A mixture of 2.00 g of polyoxyethylene glycol monostearate (4.0 E.D), 5.00 g of white emulsion type glycerin monostearate, 5.00 g of stearic acid, 1.00 g of behenyl alcohol, 10.00 g of liquid paraffin, 10.00 g of glyceryl trioctanoate and 0.20 g of ethyl p-oxybenzoate was heated to dissolve the components. Separately, purified water was added to 5.00 g of 1,3-butylene glycol to make a total of 100 g. The mixture was heated to dissolve the components. The latter solution was added to the former solution. The mixture was stirred, emulsified and cooled.

To the thus obtained emulsion were added a trace amount of fragrance and 8.00 g of purified water. The mixture was stirred and mixed to make a cream (control).

(b) A cream was obtained by formulating 1 g of kojic acid in the test sample (a) of Test Example 1(control).

(c) A cream was obtained by formulating 0.5 g of 4-(1,1-dimethyl-ethyl)-4'-methoxydibenzoylmethane in the test sample (b) of Test Example 1(composition of the present invention for external application).

(2) Method

Three regions A, B and C of 2×2 cm each were provided around the center of the inner side of the left upper arm of persons tested (46 healthy female volunteers).

An aluminum foil was set on the arm so as to expose the regions to be tested to ultraviolet rays. Two FL20S.BLB lamps and two FL20S.E-30 lamps manufactured by Toshiba Corporation were simultaneously used to irradiate the regions to be tested from a distance of 10 cm 3 times every day at a level of $0.8 \times 10^{-7}$ erg/cm$^2$/time/day. The test regions were thoroughly washed with hot water prior to the test.

Each test sample was applied to each region 3 times (morning, noon and evening) daily.

(3) Evaluation

Erythema was visually observed 3 days after the initiation of the test and pigmentation 7 and 21 days after, in comparison to the control (a), respectively, and the results were evaluated as to 4 stages.

| Stage | Points |
| --- | --- |
| No difference | — |
| Slightly thin | + |
| Obviously thin | ++ |
| Markedly thin | +++ |

(4) Results (1) Erythema (3 days after)

| | Sample (b) Case Number (%) | Sample (c) Case Number (%) |
| --- | --- | --- |
| No difference | 6 (13.0) | 0 (0.0) |
| Slightly thin | 7 (15.1) | 9 (19.6) |
| Obviously thin | 25 (54.5) | 26 (56.5) |
| Markedly thin | 8 (17.4) | 11 (23.9) |
| Total | 46 (100.0) | 46 (100.0) |

Sample (b) (control) inhibited erythema (cases with points being obviously thin or better are 71.9%) as compared to Sample (a) (control). Sample (c) (composition of the present invention for external application) inhibited erythema more than Sample (b) (cases with points being obviously thin or better are 80.4%).

(2) Pigmentation

7 Days after:

| | Sample (b) Case Number (%) | Sample (c) Case Number (%) |
| --- | --- | --- |
| No difference | 7 (15.2) | 1 (2.2) |
| Slightly thin | 6 (13.0) | 7 (15.2) |
| Obviously thin | 24 (52.2) | 27 (58.7) |
| Markedly thin | 9 (19.6) | 11 (23.9) |
| Total | 46 (100.0) | 46 (100.0) |

21 Days after:

| | Sample (b) Case Number (%) | Sample (c) Case Number (%) |
| --- | --- | --- |
| No difference | 5 (10.9) | 1 (2.2) |
| Slightly thin | 12 (26.1) | 6 (13.0) |
| Obviously thin | 26 (56.5) | 30 (65.2) |
| Markedly thin | 3 (6.5) | 9 (19.6) |
| Total | 46 (100.0) | 46 (100.0) |

Sample (b) inhibited induction of pigmentation in both tests 7 and 21 days after (cases with points being obviously thin or better are 71.8% and 63.0%, respectively) as compared to Sample (a) but Sample C provided better results than Sample (b) in both tests (cases with points being obviously thin or better are 82.6% and 84.8%, respectively).

TEST EXAMPLE 2

Sun Exposure Test

(1) Method

Three regions of 5×5 cm each were provided on the lower scapular regions of 10 normal male volunteers. Sample (a), Sample (b) and Sample (c) in Test Example 2 were applied to the regions in a dose of about 25 mg, respectively. The upper half back part of the body including each test region was exposed to direct rays of sunlight for 5 hours. The change of each test sample in coloration was observed with the passage of time.

Test conditions in this case were as follows:
Place: land owned by Fukuoka Prefecture
Weather: fine
Temperature: 24.5°–29.0° C.
Intensity of ultraviolet rays:
365 nm 4.01–4.95 mW/cm$^2$
305 nm 0.28–0.38 mW/cm$^2$
Time for exposure: 10:30–15:30

(2) Results

| | 1 Hr. After | 3 Hrs. After | 5 Hrs. After |
| --- | --- | --- | --- |
| Sample (a) | no change | slightly yellowish | some or less yellowish |
| Sample (b) | no change | slightly yellowish | some or less yellowish |
| Sample (c) | no change | no change | no change |

In Sample (a) and Sample (b), a change in color hue was noted, but in Sample (c), no change was noted at all.

The present invention is extremely useful in providing excellent compositions for external application having the effects of inhibiting erythema and pigmentation on the skin caused by ultraviolet rays after use that could not be provided by conventional kojic acid-containing compositions for external application, and thereby preventing strains or freckles due to sunburn, while at the same time preventing coloration of the compositions for external application when exposed to strong outdoor direct rays of the sun after application to the skin.

While the invention has been described in detail and with reference to specific embodiments thereof, it will be apparent to one skilled in the art that various changes and modifications can be made therein without departing from the spirit and scope thereof.

What is claimed is:

1. A composition for external application to skin to inhibit formation of erythema and pigmentation of the skin when exposed to ultraviolet light, comprising a kojic acid component selected from the group consisting of kojic acid and a kojic acid derivative, 0.01 to 5.0% by weight of the total composition of 4-(1,1-dimethylethyl)-4'-methoxydibenzoylmethane, and a carrier component.

2. A composition as in claim 1 wherein said kojic acid derivative is selected from the group consisting of a mono-fatty acid ester of kojic acid selected from the group consisting of kojic acid monopalmitate, kojic acid monobutyrate, kojic acid monocaprylate and kojic acid monostearate; a di-fatty acid ester of kojic acid selected from the group consisting of kojic acid dipalmitate, kojic acid dibutyrate, kojic acid dioleate and kojic acid distearate; kojic acid monocinnamoate; and kojic acid monobenzoate.

3. A composition as in claim 1, further comprising a UV absorbent.

4. A composition as in claim 3 wherein said UV absorbent is selected from the group consisting of a benzophenone compound selected from the group consisting of 2-hydroxy-4-methoxybenzophenone, 2-hydroxy-4-methoxybenzophenone-5-sulfonic acid and 2,2',4,4'-tetrahydroxybenzophenone; phenyl salicylate; ethyl p-aminobenzoate; ethyl urocaniate; 2-(2-hydroxy-5-methylphenyl) benzotriazole; isopropyl p-methoxycinnamate; and 2-ethylhexyl p-methoxycinnamate.

5. A composition as in claim 1, further comprising a component selected from the group consisting of an anionic substance selected from the group consisting of sodium N-lauroyl-L-glutamate and sodium dl-pyrrolidonecarboxylate; a cationic substance selected from the group consisting of stearyl chloride trimethylammonium and cetyl chloride trimethylammonium; and an antioxidant selected from the group consisting of nicotinic amide, nicotinic acid and natural vitamin E.

6. A composition as in claim 1, said composition having the property of minimum coloration when applied to the skin and exposed to ultraviolet light.

7. A composition as in claim 1, said carrier component being selected from the group consisting of a cosmetic lotion, emulsion, cream, pack and powder.

8. A composition as in claim 1, said carrier component being selected from the group consisting of an emulsion, a lotion, a liniment and an ointment.

* * * * *